(12) United States Patent
Meade

(10) Patent No.: US 6,306,149 B1
(45) Date of Patent: Oct. 23, 2001

(54) MEDICAL CLIP DEVICE WITH CYCLICAL PUSHER MECHANISM

(75) Inventor: John C Meade, Mendon, MA (US)

(73) Assignee: Microline, Inc., Beverly, MA (US)

( * ) Notice: Subject to any disclaimer, the term of this patent is extended or adjusted under 35 U.S.C. 154(b) by 0 days.

(21) Appl. No.: 09/504,498

(22) Filed: Feb. 15, 2000

(51) Int. Cl.[7] .................................................. A61B 17/04
(52) U.S. Cl. .................................................. 606/143
(58) Field of Search .................... 606/142, 143; 227/19

(56) References Cited

U.S. PATENT DOCUMENTS

| | | | |
|---|---|---|---|
| Re. 36,720 | * | 5/2000 | Green et al. .......................... 606/151 |
| 3,638,847 | * | 2/1972 | Noiles ................................... 606/143 |
| 4,522,207 | * | 6/1985 | Klieman et al. ...................... 606/143 |
| 4,674,504 | * | 6/1987 | Klieman et al. ...................... 606/143 |
| 5,246,450 | * | 9/1993 | Thornton et al. ..................... 606/143 |
| 5,626,585 | * | 5/1997 | Mittelstadt et al. .................. 606/143 |
| 5,772,673 | * | 6/1998 | Cuny et al. ........................... 606/142 |
| 6,059,799 | * | 5/2000 | Aranyi et al. ........................ 606/143 |

* cited by examiner

Primary Examiner—Gary Jackson
(74) Attorney, Agent, or Firm—Don Halgren

(57) ABSTRACT

The present invention relates to a clip feeder arrangement for supportive receipt in a handle of a medical clip stapling gun, for the advancement of a plurality of clips seriatim by a trigger mechanism in the handle to a location between a pair of pincher jaws. A distalmost clip of the plurality of clips is advanced to the jaws prior to advancement of the remaining plurality of clips. The feeder arrangement comprises a U-shaped cartridge having a proximal end and a distal end, the cartridge containing the plurality of clips, a frame for supporting the cartridge and an elongated, cyclically movable feeder bar or pusher mechanism arranged beneath and enagable with the cartridge, for first advancing the distalmost clip in the cartridge to a location between the jaws and then subsequently advancing the remaining plurality of clips distally by a ladder pushed thereadjacent, both of the advancement motions occurring in a single distal advance of the feeder bar mechanism.

19 Claims, 4 Drawing Sheets

MEDICAL CLIP DEVICE WITH CYCLICAL PUSHER MECHANISM

BACKGROUND OF THE INVENTION

1. Field of the Invention

This invention relates to feeding arrangements for medical clip and stapling devices, particularly for the pinching or clipping of blood vessels or for the closure of wounds, and is related to commonly owned, co-pending U.S. application Ser. No.: 09/504,572 filed Feb. 15, 2000, entitled "Ladder-Type Medical Feeding Mechanism", and incorporated herein by reference in its entirety.

2. Prior Art

Clips and surgical staplers have been used by physicians to replace suturing and for closing wounds or to tie-off blood vessels during a surgical procedure or other traumatic medical event. Such surgical clips and stapler applicators generally comprise of closed jaws, which crimp a U-shaped clip flat across the tissues to be tied or sutured. Typically, such an application device is arranged through the spaced clips in a sequential manner, those clips being fed serially to the jaws.

The tools typically in use dispense such clips to the jaws sequentially, the distalmost clip being pinched, and the next adjacent clip immediately therebehind being advanced immediately adjacent the pinched clip. Examples of such clip feeding arrangements are shown in U.S. Pat. No. 5,246,450 to Thornton et al, showing a clip feeding and dispenser mechanism which uses a spring to force the movement of clips in line with an applicator.

The U.S. Pat. No. 3,638,847 to Noiles et al, shows a ratchet driven cartridge for advancing sequentially a plurality of staples. U.S. Pat. No. 5,626,585 to Mittelsteate et al, shows a ligating clip advancing device for advancing a plurality of clips along a track between a pair of pinched jaws. The U.S. Pat. No. 4,674,504 to Klieman et al, shows a spring activated homeostatic clip applicator wherein a double ratchet apparatus advances clips through a magazine to cause a clip-feed blade to slide through the magazine to place a clip in the deforming jaws. Each of the above identified prior art patents is incorporated herein by reference in their entirety.

It is an object of the present invention, to provide a medical clip feeding mechanism which is an improvement over the prior art.

It is a further object of the present invention, to provide a medical clip feeding mechanism which advances the distalmost clip into the jaws of the stapling device prior to the advancement of the next available clip moving along the feed track.

It is yet a still further object of the present invention, to provide a simple and easy to use clip feeder arrangement which is tolerant of slight dimensional irregularity in the clips or staplers utilized by the stapling device or gun and cycles the drive mechanism to engage and disengage the clips and their pusher member.

BRIEF SUMMARY OF THE INVENTION

The present invention relates to a clip or staple feeding arrangement for providing clips or staples to the jaws of a medical stapling gun. The new staple clip gun comprises a handle at one end thereof, for holding and actuating the clip stapling arrangement. The handle comprises a housing and a trigger mechanism for actuating the jaws and clip feeding mechanism. The housing has an opening through which the proximal end of a barrel is supported. The barrel has a distal end where the jaws, utilized for feeding and pinching the clips or staples, is located. A generally U-shaped frame member is arranged through the length of the inside of the barrel. The frame member has a plurality of bridges spaced along its elongated length. A jaw control rod, moveable proximally and distally, is supportively arranged upon those bridges, to provide the pinching movement to the jaws at the distal end of the barrel. The frame has several portions along its length on its lowermost side, having elongated slots therein. The distalmost slot is arranged near the distal end of the barrel, and a mid-slot is arranged along a mid portion of the frame's length. A ramp-like projection is arranged at a location on each side of the distalmost and the mid-portion slot in the frame, which ramp acts as a cam track to guide pins extending transversely from the sides of upstanding fingers of an elongated, spring stainless steel clip feeder bar into engagement with the distalmost clip and the elongated, slotted ladder respectively. The elongated, slotted ladder pushes all but the distalmost clip distally along in the frame.

The barrel is arranged to receive a clip cartridge at its rearmost opening at the housing in the handle. The frame is arranged to receive a clip or stapler cartridge which includes an elongated ladder, through an opening in the rearside of the handle. The clips are generally U-shaped, and have leg members which extend distally from the housing. The clips and the elongated ladder are arranged to be slidable within the generally U-shaped channel, the channel providing their enclosure in the package. The elongated ladder has a plurality of elongated slots or holes of generally rectangular shape which holes are arranged longitudinally down the middle portion thereof. The ladder has a distal end, which abuts the last (proximalmost) clip within the cartridge.

The cartridge in each of the preferred embodiments of the present invention contains about twenty U-shaped clips or staples seriatim therein. Each clip is in an abutting and in a pushing relationship with its adjacent distal clip.

The elongated cycling clip pusher or feeder bar is arranged within the barrel and supported beneath the frame member therewithin. The cycling clip pusher or feeder bar has a distalmost finger projecting towards the cartridge, and having a pin extending from each transverse side thereof. The clip pusher or feeder bar also has a proximal finger extending upwardly in a spaced relation to the elongated slot location in the lowermost side of the mid-portion of the frame member. The elongated cycling clip pusher or feeder bar is advancable distally and returnable proximally in a cyclic manner responding to the actuation of the trigger mechanism within the handle of the clip device. The proximate finger also has a pin extending transversely from each side thereof in a manner similar to that of the distalmost finger.

Movement of the trigger mechanism cycles the longitudinal distal advancement of the elongated clip pusher or feeder bar relative to the frame member. As the proximal finger is advanced simultaneously with the distal finger, the proximal finger is biasedly permitted by the spring nature of the stainless steel clip feeder to enter the hole of the elongated ladder corresponding to the location of the opening in the lower portion of mid-portion of the frame. The same longitudinal advance of the clip pusher or feeder bar effects simultaneous distal advancement of the distal finger. As the distalmost finger advances, its spring-like bias pushes it into the slot in the frame where permitted by the pins cammed with the ramp-like tracks. The distal finger then touches the backside of the distalmost clip, to push it distally and thereby to effect its entry between the pincher jaws. The trigger mechanism then effects the squeezing together of the pincher jaws by advancing the crimp box pushed by the pusher rod, to crimp the clip or staple onto a body component to be pinched close. The trigger mechanism also simultaneously continues to advance the proximal finger on the clip feeder bar, which proximal finger has traveled the length of the rectangular hole in the ladder at its location adjacent its opening in the frame member. As the proximal finger enters the rectangular hole in the ladder, the proximal finger moves within that rectangular hole until it comes to a bar across the distal end of that hole, where it then begins to push the ladder distally a spaced distance, to then make the ladder push upon all of the series of clips within the cartridge, thus effecting delivery of the next available clip to its "stand-by" position at the distal end of the frame.

Squeezing of the trigger mechanism effects the rearward or proximate cycle of movement of the clip pusher or feeder bar in a proximal direction, the side pins of each respective finger engaging the ramp walls of the lower side of the slot on the lower side of the frame member, so as to also bias downwardly the fingers out of the way of the respective clips and ladder openings or holes thereadjacent. Thus, an oval cyclical path is taken by the clip feeder bar. The generally oval path is thus generated by the ramp-like fingers, the upper side of the oval path comprising the fingers biased into engagement with the ladder and the distalmost clip respectively, and the lower side of the oval path being traveled by the fingers and their clip feeder bar to their proximalmost position to await re-activation and re-cycling by the trigger in the handle. The clip feeder bar (with its fingers) is thus returned to its distalmost location to await a further actuation of the trigger, which would recycle the feeder bar mechanism and advance the clips accordingly.

Operation of the device is as follows: Squeezing of the trigger mechanism in the handle cycles the longitudinal distal advancement of the elongated clip feeder relative to the frame member. Release of the trigger simultaneously advances the proximal finger with the distal finger, the proximal finger is permitted by the spring action of the clip feeder, and the ramp-like tracks on the side of the slot in the frame, to enter the hole of the elongated ladder corresponding to the location of the opening in the lower portion of mid portion of the frame. The same longitudinal advance of the clip feeder effects simultaneous advancement of the distal finger. As the distalmost finger advances, its spring like bias pushes it into the slot in the frame where permitted by the ramp-like tracks. The distal finger then touches the backside of the distalmost clip, to push it distally and effect its entry between the pincher jaws. The trigger mechanism effects the squeezing together of the open pincher jaws by distally advancing a crimp box on the push rod to crimp the clip or staple onto a body component to be pinched close.

Release of the trigger mechanism also opens the jaws and advances the proximal finger on the clip feeder member, which finger has traveled the length of the rectangular slot or hole in the ladder at its location adjacent its opening in the framed member. As the proximal finger enters the distal end of that rectangular hole in the ladder, it continues to move within that rectangular hole until it comes to the distal end of that hole, where it then begins to push the ladder distally a spaced distance, to then also push upon the series of clips within the cartridge, thus effecting delivery of the next available clip to its stand-by position at the distal end of the frame. Squezzing of the trigger mechanism effects the rearward or proximate cycle of movement of the clip feeder bar proximally, and the side pins of each respective finger engaging the ramp walls of the lower side of the slot on the frame member, so as to also bias downwardly the fingers out of the way of the respective clips and ladder openings or holes thereadjacent. A generally oval path is thus generated by the fingers, the upper side of the oval path comprising the fingers engaging the ladder and the distalmost clip respectively, and the lower side of the oval path being traveled by the fingers and their clip feeder member returning to their proximalmost position to await re-activation by the trigger in the handle. The clip feeder bar is thus returned to its proximalmost location to await a further actuation of the trigger, which would recycle the feeder bar mechanism and advance the clips accordingly.

When the trigger is in the "relaxed" position (after one actuation), the jaws are open and the cinch box is in is proximalmost location. The distalmost finger has pushed a clip between the jaws and the proximal finger has pushed the ladder "one stop" distally, pushing all the clips including the distalmost clip to the end of the cartridge. When the trigger is squeezed, the push rod is advanced to advance the cinch box, to close the jaws. Both fingers are cammed downwardly by virtue of the side pins engaging the ramps adjacent the slot in the frame, so as to move out of the way from hitting the next distalmost clip and out of the way of the ladder as the fingers are pulled proximally. When the trigger is released, the cinch box is caused to retract, permitting the jaws to bias themselves open, and then the clip feeder bar pushes a new distal clip into the jaws, and then the proximal finger pushes the ladder and the whole series of clips distally.

The invention thus comprises a clip feeder arrangement for supportive receipt in a handle of a medical clip stapling gun for the advancement of a plurality of clips seriatim by a trigger mechanism in the handle to a location between a pair of pincher jaws. A distalmost clip of the plurality of clips is advanced to the jaws prior to advancement of the remaining plurality of clips. The feeder arrangement comprises a U-shaped cartridge having a proximal end and a distal end, the cartridge containing the plurality of clips insertable through the rear of the housing, a frame for supporting the cartridge, an elongated, a cyclically movable clip pusher/feeder mechanism arranged beneath and engageable with the cartridge, for first advancing the distalmost clip in the cartridge to a location between the jaws and then subsequently advancing the remaining plurality of clips distally by a ladder pushed thereadjacent, both of the advancement motions occurring in a single distal advance of the pusher mechanism. The pusher mechanism comprises a clip feeder bar, the clip feeder bar having a distal finger and a proximal finger thereon, wherein the distal finger pushes the distalmost clip to a location between the pair of jaws. The proximal finger while advancing distally pushes the ladder to push the remaining clips in the cartridge after the distalmost clip has entered between the jaws. The distal finger is of extended tab-like configuration with side pins cammed on ramps adjacent the slot in the frame, to permit its cammed displacement from engagement with the clips during its return to its starting position below the frame. The proximal finger is of extended tab-like configuration with side pins engagable with the ramps, to similarly permit its cammed displacement from engagement with the ladder during its return to its starting position below the frame. The frame has a clip feeder guide plate therebeneath, to support the fingers during a portion of the movement of the fingers and the clip feeder bar with respect to the frame. Each of the fingers having their pair of pins which extend transversely therefrom, to cam the fingers into and out of engagement with the clips and the ladder. Actuation of the trigger mechanism is arranged with the clip feeder bar to actuate advancement of the distalmost clip into the jaws and subsequent distal advancement of the clips in the cartridge towards the jaws during a single stroke of the trigger. An elongated barrel encloses the mechanism, to enclose and protect the clip feeder mechanism therewithin. The barrel is supported in an opening in the handle for communication of the trigger mechanism and the clip feeder mechanism. The clips may be of slight differing dimensions within the cartridge, and may be fed to the gun through an opening in the rearside of the handle.

The invention also includes a method of advancing seriatum a plurality of clips in a cartridge in a medical clip stapling gun by a manual single-pull trigger mechanism in a handle of the stapling gun. A distalmost clip of the plurality of clips is advanced to a set of jaws in the distal end of the stapling gun by the steps of: advancing the distalmost clip from the cartridge by engaging a clip feeder bar therewith in a distal motion, the feeder bar being connected to the trigger; and subsequently advancing the plurality of clips in the cartridge distally by engaging the feeder bar therewith during the distal motion after the distalmost clip is disposed between the jaws and during the release of the trigger. The steps include cycling the distal finger out of engagement with the distalmost clip during a return path of the feeder bar, cycling the feeder bar out of engagement with the plurality of clips in the cartridge during a return path of the feeder bar, arranging a distal finger projection on the feeder bar so as to engage the distalmost clip, arranging a second finger projection on the feeder bar so as to engage a ladder engaging the clips in the cartridge, extending a pair of pins transversely from each projection to facilitate a camming of the fingers away from the clips during the return path of the feeder bar, arranging a ladder in the cartridge for the engagement with the proximal or second finger projection so as to push the clips during distal advance of the second finger, and arranging an elongated opening in the ladder in the cartridge to permit delayed engagement thereof with the second finger projection.

Thus what has been shown as a unique feeder mechanism for supplying a plurality of clips or staples in a sequential manner, wherein the distalmost clip is advanced into a pair of squeezeable jaws by a cycling feeder bar before a next adjacent clip is fed forward into its stand-by location. Engagement by the proximalmost finger of the feeder bar into an elongated slot of the ladder permits a tolerance of slight dimensional inadequacy within a respective clips or staples within the series of staples maintained within the cartridge and delays the distal advance of the remaining clips in the cartridge until the first or distalmost clip is between the jaws of the device.

BRIEF SUMMARY OF THE DRAWINGS

The objects and advantages of the present invention will become more apparent, when viewed in conjunction with the following drawings, in which.

DESCRIPTION OF THE PREFERRED EMBODIMENTS

Figure 1:
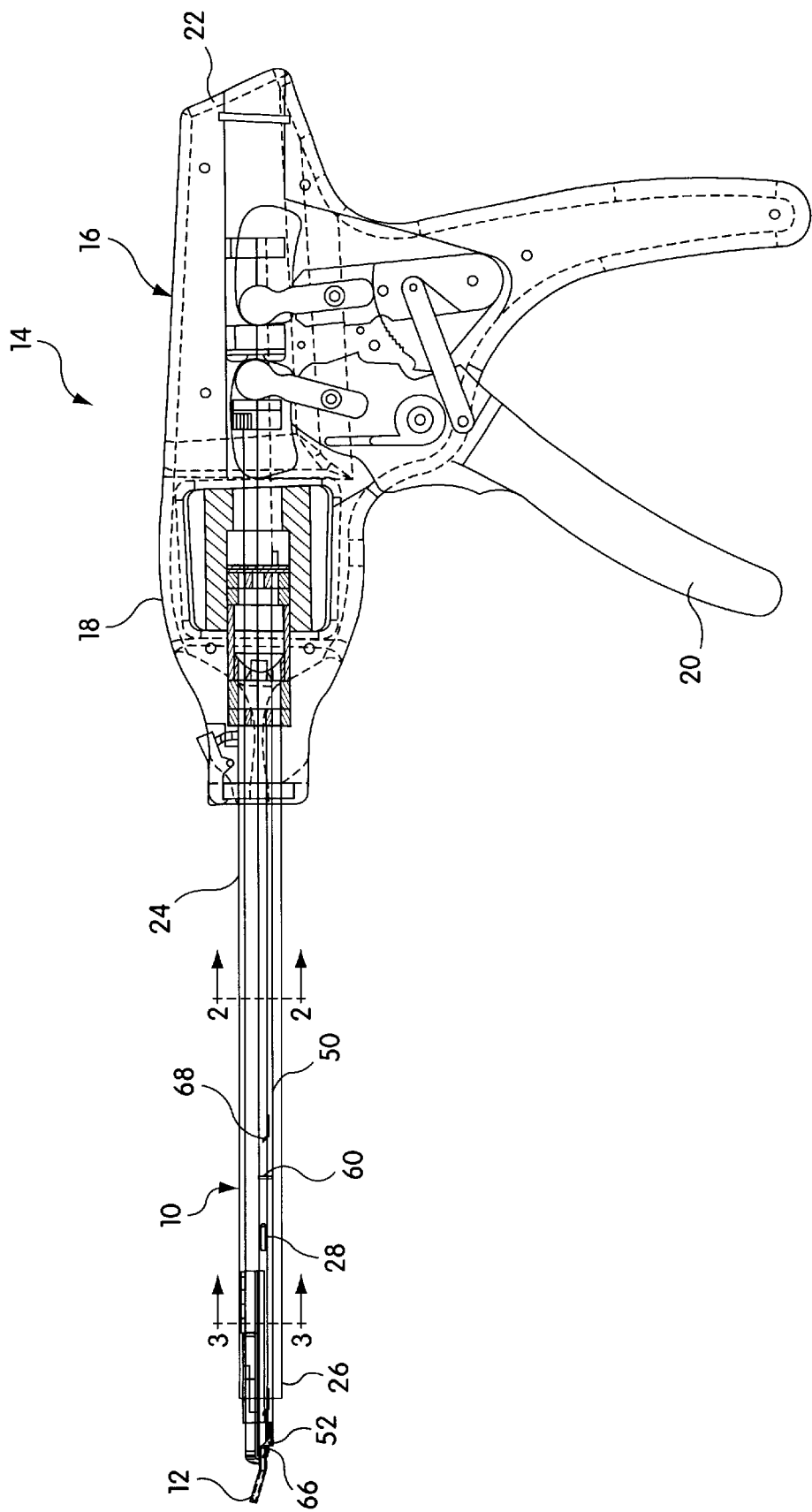
FIG. 1 is a side elevational view, partly in section, of a homeostatic clip delivery gun respective according to the principals of the present invention.
Figure 2:
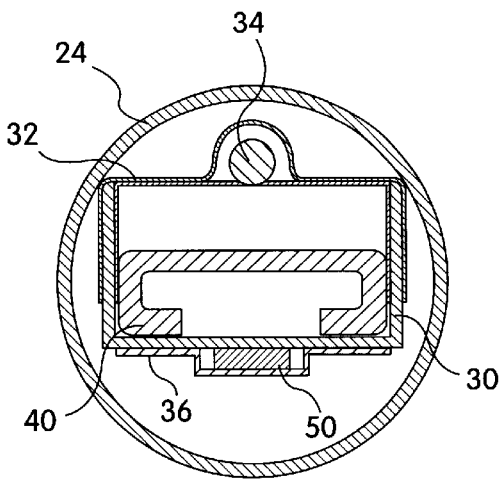
FIG. 2 is cross sectional view taken along the lines 2—2 of FIG. 1.
Figure 3:
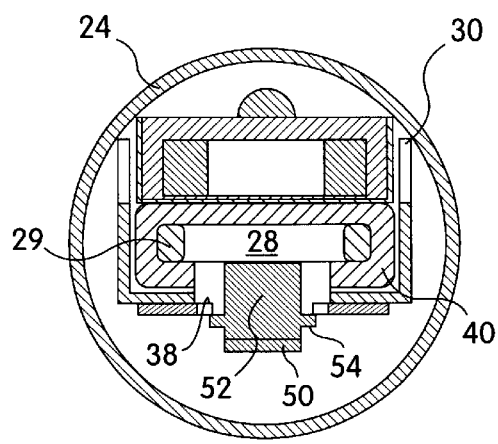
FIG. 3 is a cross section view taken along the lines 3—3 of FIG. 1.
Figure 4:
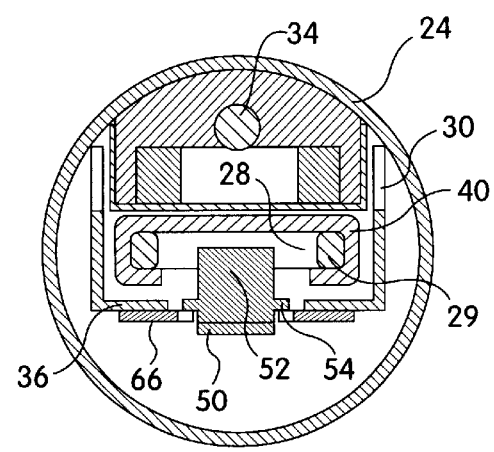
FIG. 4 is a view similar to FIG. 3, showing the feeder dyed finger in its engagement orientation.
Figure 5:
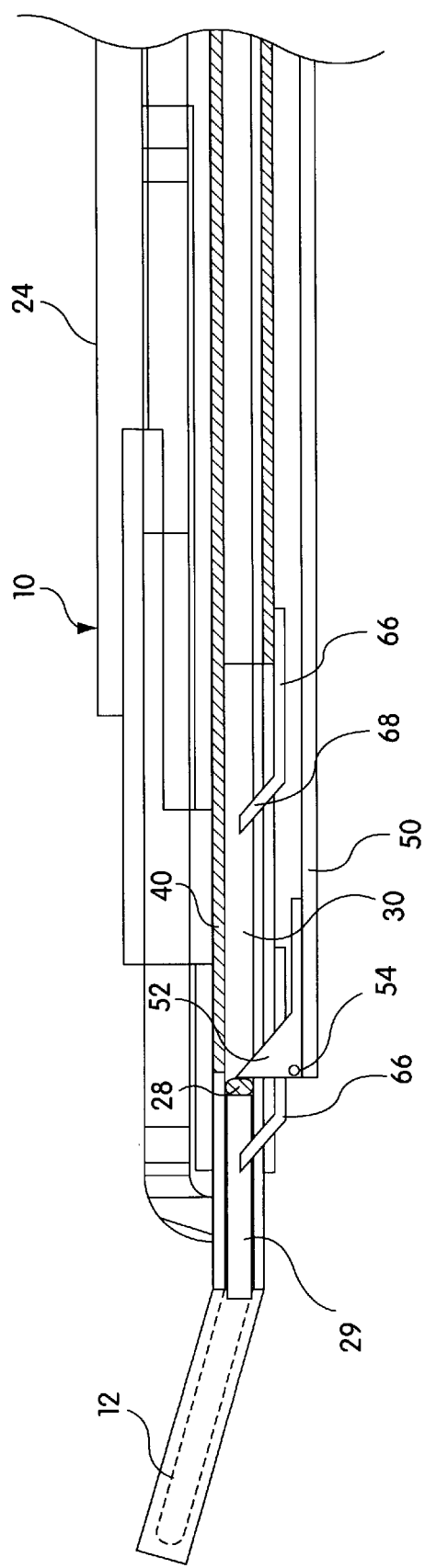
FIG. 5 is a sectional view of the distal most end of the feeder apparatus.

Referring now to the drawings in detail, and particularly to FIG. 1, there is shown the present invention which comprises a clip or staple advancing and feeding arrangement 10 for providing clips or staples to the jaws 12 of a medical stapling gun 14. The staple clip gun 14 comprises a handle 16 at a first end thereof, for holding and actuating the clip stapling arrangement 10. The handle 16 comprises a housing 18 and a trigger mechanism 20 for actuating the jaws 12 and the clip feeding mechanism 10. The housing 18 has an opening 22 through which a proximal end of a barrel 24 is supported. The barrel 24 has a distal end 26 where the jaws 12, utilized for feeding and pinching the clips or staples 28, is located. A generally U-shaped frame member 30, shown more clearly in FIGS. 2, 3, 4 and 6, is arranged through the length of the inside of the barrel 24. The frame 30 has a plurality of spaced apart bridges 32 extending along its elongated length. A jaw control rod 34, moveable proximally and distally, is supportively arranged on the bridges 32, as may be seen in FIG. 2, to provide the pinching movement to the jaws 12 at the distal end 26 of the barrel 24. The frame 30 has several portions along its length on its lower-most side 36, having elongated slots 38 therein, as may be seen in FIGS. 3, 4 and 6. The distalmost slot 38'is arranged near the distal end 26 of the barrel 24, and a mid-slot 38"is arranged along a mid portion of the frame's length, as may be seen in FIG. 6.

Figure 6:
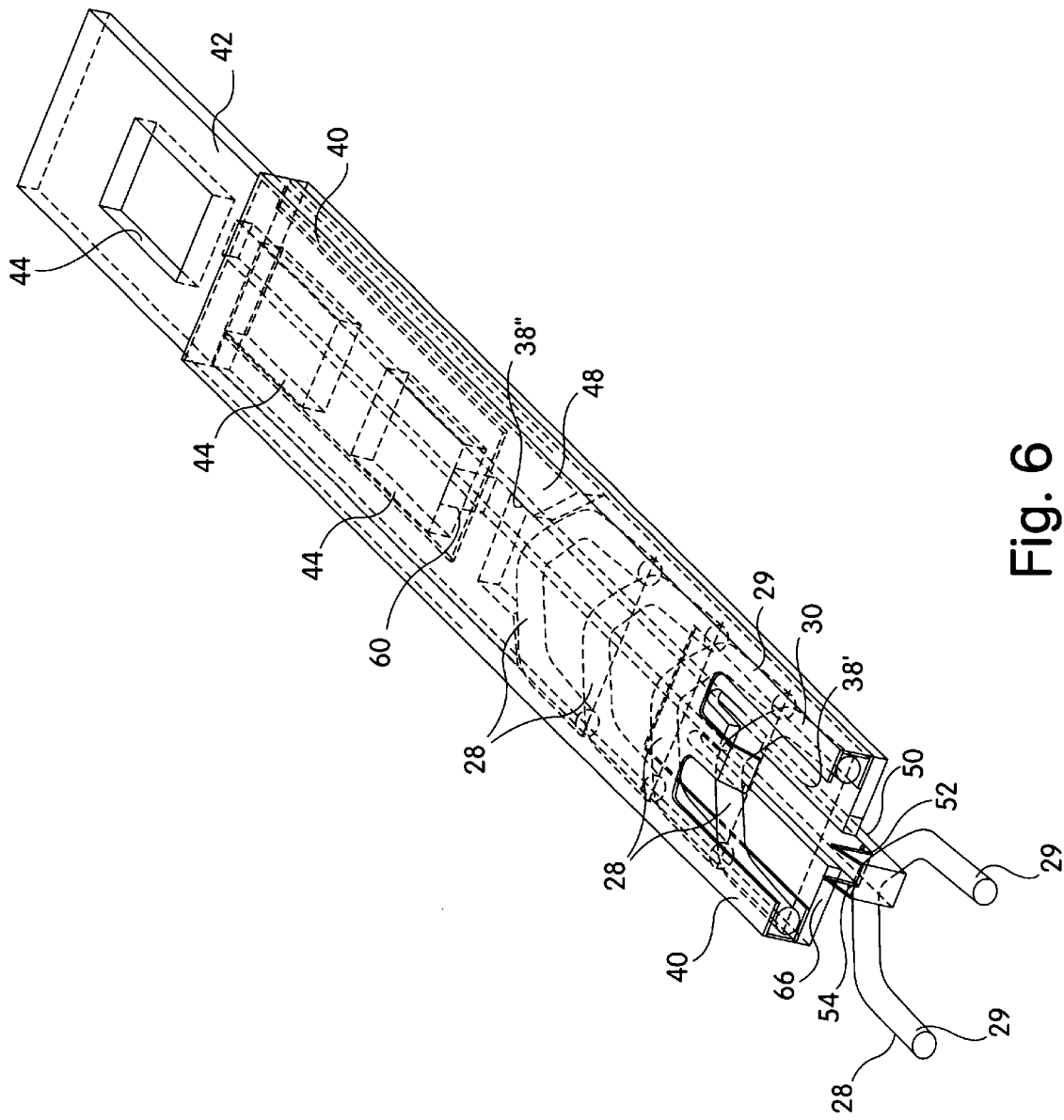
FIG. 6 is a view, in perspective of the feeder cartridge.

The barrel 24 is arranged to receive a clip cartridge 40 at its rearmost opening 22 at the housing 18 in the handle 16. The frame 30 is arranged to receive the U-shaped (cross-section) clip or stapler cartridge 40 which includes a plurality of clips or staples 28 and an elongated ladder 42, which is best seen in FIG. 6. The clips 28 are generally U-shaped, and have leg members 29 which extend distally away from the housing 18. The clips 28 and the elongated ladder 42 are arranged to be slidable within the generally U-shaped cartridge 40, which provides their enclosure in the package. The elongated ladder 42 has a plurality of elongated holes 44 of generally rectangular shape arranged longitudinally down the middle portion thereof, as may be seen in FIG. 6. The ladder 42 has a distal end 48, which abuts the last (proximalmost) clip 28 within the cartridge 40.

In each of the preferred embodiments of the present invention, about twenty U-shaped clips or staples 28 may be held seriatim in the cartridge 40. Each clip 28 is in an abutting and in a pushing arrangement with its adjacent distal clip 28, as shown in FIG. 6.

An elongated cycling clip pusher or feeder member or bar 50 is arranged within the barrel 24 and is supported beneath the frame member 30 therewithin. The clip pusher or feeder member or bar 50 has a distalmost finger 52 of ramp-like configuration, having a short pin 54 extending from each transverse side thereof, as may be seen in FIGS. 3, 4 and 6. The cycling clip pusher or feeder bar 50 also has a proximal finger 60 extending upwardly in a spaced relation to the elongated slot location in the lowermost side of the frame member 30, as may be seen in a side view in FIG. 6. The elongated clip pusher or feeder bar 50 is movable distally and proximally according to the actuation of the trigger mechanism 20 within the handle 16 of the medical clip gun device 14. The proximate finger 60 also has a pin (not shown for clarity), extending transversely from each side thereof in a manner similar to that of the distalmost finger 52. The pins 54 on the fingers 52 and 60 cause the fingers to be cammed out of engagement with the clips 28 and ladder 42 through sliding engagement with the ramps 66 and 68 adjacent the slots 38 in the frame member 30, as the feeder bar 50 is drawn proximally.

Releasing of the trigger mechanism 20 cycles the longitudinal distal advancement of the elongated clip pusher or feeder bar 50 relative to the frame member 30. As the proximal finger 60 is advanced simultaneously with the distal finger 52, the proximal finger 60 is permitted by the upward spring action thereof and camming of the pins 54 on the sides of the finger 60, to enter one of the holes 44 of the elongated ladder 42 corresponding to the location of the slot opening 38" in the lower mid portion of the frame 30, as embodied in FIG. 1, and shown in FIG. 6. The same advance of the clip pusher or feeder bar 50 also effects corresponding distal advancement of both the distal finger 52 and the proximal finger 60. As the distalmost finger 52 advances it engages the backside of the distalmost clip 28, as represented in FIG. 6, to push upon thereon and effect its entry between the pincher jaws, (not shown in FIG. 6, for clarity). The trigger mechanism 20 effects the squeezing together of the open pincherjaws 12 to crimp the clip or staple 28. The trigger mechanism 20 also continues to advance the pusher bar 50 and its proximal finger 60, which has by then traveled the length of the rectangular hole 44 in the ladder 42 at its location adjacent its opening 38" in the frame member 30. As the proximal finger 60 engages the distal end of that rectangular hole 44 in the ladder 42, it then begins to push the ladder 42 distally a spaced distance, to push upon the entire series of clips 28 within the cartridge 40 thus effecting delivery of the next available staple or clip 28 to its "stand-by" position at the distal end 26 of the barrel 24 after the former distalmost clip 28 has been pushed between the jaws 12 by the distalmost finger 52.

Squeezing of the trigger mechanism 20 effects downward and rearward or proximate cycle of movement of the clip feeder bar 50, (as indicated by the dashed arrows "C" in FIG. 1) and the side pins 54 of each respective finger 52 and 60 engaging the lower side of the slot 38 on the lower side of the frame member 30, so as to bias the fingers 52 and 60 down and out of the way of the respective clips 28 and ladder openings or holes 44 respectively thereadjacent as the clip pusher or feeder bar 50 cycles rearwardly completing a generally "oval" path "C". The clip pusher or finger bar 50 is then returned to its proximalmost location with the pins 54 riding under the feeder guide plate 66, to await a further actuation of the trigger mechanism 20, which would recycle the entire clip cartridge 20 and feeder bar mechanisms 50 accordingly.

Thus what has been shown as a unique feeder mechanism for supplying a plurality of clips or staples in a sequential manner, wherein the distalmost clip is advanced into a pair of squeezable jaws before a next adjacent clip is fed forward into its stand-by location. Engagement by the proximalmost fingers into an elongated slot before the ladder is forced to move while the distalmost finger advances the distalmost clip permits a tolerance of dimensional inadequacy with respective clips or staples within the series of staples maintained within the cartridge and sequential displacement of clips with one common distal movement of the cyclical feeder bar.

What is claimed is:

1. A clip feeder arrangement for supportive receipt in a handle of a medical clip stapling gun, for the advancement of a plurality of clips seriatim by a trigger mechanism in said handle to a location between a pair of pincher jaws, a distalmost clip of said plurality of clips being advanced to said jaws prior to advancement of the remaining plurality of clips, said feeder arrangement comprising:
   a U-shaped cartridge having a proximal end and a distal end, said cartridge containing said plurality of clips;
   a frame for supporting said cartridge;
   an elongated, cyclically movable feeder mechanism arranged beneath and engagable with said cartridge, for first advancing said distalmost clip in said cartridge to a location between said jaws and then subsequently advancing said remaining plurality of clips distally by a ladder pushed thereadjacent, both of said advancement motions occurring in a single distal advance of said feeder mechanism.

2. The clip feeder mechanism as recited in claim 1, wherein said feeder mechanism comprises a clip feeder bar, said clip feeder bar having a distal finger and a proximal finger thereon, wherein said distal finger pushes said distalmost clip to a location between said pair of jaws.

3. The clip feeder mechanism as recited in claim 2, wherein said proximal finger pushes said ladder to push said remaining clips in said cartridge after said distalmost clip has entered between said jaws.

4. The clip feeder mechanism as recited in claim 3, wherein said distal finger is cammed to permit its displacement from engagement with said clips during its return to its starting position below said frame.

5. The clip feeder mechanism as recited in claim 3, wherein said proximal finger is cammed to permit its displacement from engagement with said ladder during its return to its starting position below said frame.

6. The clip feeder mechanism as recited in claim 4, wherein said frame has a clip feeder guide plate therebeneath, to support said fingers during a portion of said movement of said fingers and said clip feeder bar with respect to said frame.

7. The clip feeder mechanism as recited in claim 4, wherein each of said fingers have a pair of pins extending transversely therefrom to cam said fingers into and out of engagement with said clips and said ladder.

8. The clip feeder mechanism as recited in claim 4, wherein actuation of said trigger mechanism is arranged with said clip feeder bar to actuate advancement of said distalmost clip into said jaws and subsequent distal advancement of said clips in said cartridge towards said jaws during a single stroke of said trigger.

9. The clip feeder mechanism as recited in claim 4, wherein an elongated barrel encloses said mechanism, to enclose and protect said clip feeder mechanism therewithin.

10. The clip feeder mechanism as recited in claim 9, wherein said barrel extends through an opening in said handle for communication of said trigger mechanism and said clip feeder mechanism.

11. The clip feeder mechanism as recited in claim 9, wherein said clips are of differing dimensions within said cartridge.

12. The clip feeder mechanism as recited in claim 7, wherein said frame includes a plurality of ramps which are engagable with said pins in said fingers, to cam said feeder bar into and out of engagement with said clips and said ladder.

13. A method of advancing seriatum a plurality of clips in a cartridge in a medical clip stapling gun by a manual single-pull trigger mechanism in a handle of said stapling gun, with a distalmost clip of said plurality of clips being advanced to a set of jaws in a distal end of said stapling gun comprising the steps of:

advancing said distalmost clip from said cartridge by engaging a pusher bar therewith in a distal motion, said pusher bar being connected to said trigger;

subsequently advancing said plurality of clips in said cartridge distally by engaging said pusher bar therewith during said distal motion, after said distalmost clip is disposed between said jaws and during said single pull of said trigger; and cycling said pusher bar out of engagement with said distalmost clip during a return path of said pusher bar.

14. The method of advancing seriatum a plurality of clips in a cartridge in a medical clip stapling gun by a manual single-pull trigger mechanism in a handle of said stapling gun, as recited in claim 13, including the step of:

cycling said pusher bar out of engagement with said plurality of clips in said cartridge during a return path of said pusher bar.

15. The method of advancing seriatum a plurality of clips in a cartridge in a medical clip stapling gun by a manual single-pull trigger mechanism in a handle of said stapling gun, as recited in claim 13, including the step of:

arranging a finger projection on said pusher bar so as to engage said distalmost clip.

16. The method of advancing seriatum a plurality of clips in a cartridge in a medical clip stapling gun by a manual single-pull trigger mechanism in a handle of said stapling gun, as recited in claim 14, including the step of:

arranging a second finger projection on said pusher bar so as to engage said clips in said cartridge.

17. The method of advancing seriatum a plurality of clips in a cartridge in a medical clip stapling gun by a manual single-pull trigger mechanism in a handle of said stapling gun, as recited in claim 15, including the step of:

extending a pair of pins transversely from each projection to facilitate a camming of said fingers away from said clips during said return path of said pusher bar.

18. The method of advancing seriatum a plurality of clips in a cartridge in a medical clip stapling gun by a manual single-pull trigger mechanism in a handle of said stapling gun, as recited in claim 16, including the step of:

arranging a ladder in said cartridge for said engagement with said second finger projection so as to push said clips during distal advance of said second finger.

19. The method of advancing seriatum a plurality of clips in a cartridge in a medical clip stapling gun by a manual single-pull trigger mechanism in a handle of said stapling gun, as recited in claim 18, including the step of:

arranging an elongated opening in said ladder in said cartridge to permit delayed engagement thereof with said second finger projection.

* * * * *